US011638780B1

(12) United States Patent
Howard et al.

(10) Patent No.: US 11,638,780 B1
(45) Date of Patent: May 2, 2023

(54) MEDICAL DRAINAGE PUMP

(71) Applicants: Robert Howard, Centerville, OH (US);
Randy Hinders, Centerville, OH (US)

(72) Inventors: Robert Howard, Centerville, OH (US);
Randy Hinders, Centerville, OH (US)

( * ) Notice: Subject to any disclaimer, the term of this patent is extended or adjusted under 35 U.S.C. 154(b) by 0 days.

(21) Appl. No.: 17/933,694

(22) Filed: Sep. 20, 2022

Related U.S. Application Data

(63) Continuation-in-part of application No. 17/707,932, filed on Mar. 29, 2022, now abandoned.

(51) Int. Cl.
*A61M 1/00* (2006.01)
*A61M 27/00* (2006.01)

(52) U.S. Cl.
CPC .............. *A61M 1/82* (2021.05); *A61M 27/00* (2013.01)

(58) Field of Classification Search
CPC ........ F04B 45/08; F04B 45/085; F04B 45/10; F04B 43/12; F04B 43/1215; F04B 43/123; F04B 43/1238; F04B 43/1253; F04B 43/1269; F04B 43/1276; F04B 43/1284; B05B 9/0872; B05B 9/042
See application file for complete search history.

(56) References Cited

U.S. PATENT DOCUMENTS

| 4,205,948 | A | * | 6/1980 | Jones | F04B 43/1253 |
| | | | | | 417/477.6 |
| 4,661,093 | A | * | 4/1987 | Beck | A61M 27/00 |
| | | | | | 604/152 |
| 6,149,621 | A | * | 11/2000 | Makihara | F04B 43/1284 |
| | | | | | 604/27 |
| 2004/0096347 | A1 | * | 5/2004 | Pelmulder | F04B 43/1238 |
| | | | | | 417/476 |
| 2005/0047925 | A1 | * | 3/2005 | Davis | F04B 43/1253 |
| | | | | | 417/53 |
| 2005/0056666 | A1 | * | 3/2005 | Erlandsen | A47J 47/01 |
| | | | | | 222/527 |
| 2007/0207041 | A1 | * | 9/2007 | Gao | F04B 43/0081 |
| | | | | | 417/477.2 |
| 2009/0214365 | A1 | * | 8/2009 | Norman | A61M 5/14232 |
| | | | | | 417/474 |
| 2010/0054975 | A1 | * | 3/2010 | Ibragimov | A61M 60/441 |
| | | | | | 417/477.3 |
| 2014/0010675 | A1 | * | 1/2014 | Kent | F04B 43/1238 |
| | | | | | 417/476 |
| 2015/0104330 | A1 | * | 4/2015 | Chin | F04B 43/10 |
| | | | | | 417/320 |
| 2017/0268496 | A1 | * | 9/2017 | McIntyre | F04B 43/1261 |
| 2017/0314545 | A1 | * | 11/2017 | Choi | F04B 43/1215 |
| 2018/0117239 | A1 | * | 5/2018 | Schmidt | A61M 3/0258 |
| 2018/0128266 | A1 | * | 5/2018 | Gaskill-Fox | F04B 43/0072 |
| 2018/0230988 | A1 | * | 8/2018 | Fang | F04B 43/0072 |
| 2019/0298896 | A1 | * | 10/2019 | Charlez | F04B 43/1261 |

* cited by examiner

*Primary Examiner* — Adam Marcetich
(74) *Attorney, Agent, or Firm* — RC Trademark Company

(57) ABSTRACT

According to some embodiments, a drain line milking apparatus is disclosed. The drain line milking apparatus includes an apparatus body comprising a plurality of side opening for receiving a currently connected drain line to milk fluids away from a user, a removable cover disposed over the apparatus body, a circular disk comprising one or more cam openings, a motor to turn the circular disk and one or more circular cams disposed in the one or more cam openings. The circular disk is disposed within the apparatus body.

13 Claims, 4 Drawing Sheets

200

300

MEDICAL DRAINAGE PUMP

BACKGROUND

Pathogens, such as the novel coronavirus (COVID-19) may be spread through aerosols and respiratory droplets that are expelled from a person's mouth or nose when an infected person talks, coughs or sneezes. For patients that are required to remain in a hospital setting while recovering, the risk of contamination is greater than recovery at home. Patients recovering from surgery often require the use of a medical drainage pump which may require the patent to remain in the hospital thus increasing their exposure to COVID-19. Therefore, a medical drainage pump that allows patients to recover at home, and away from the risks of COVID-19, is desirable.

SUMMARY

Some embodiments described herein relate to a drain line milking apparatus. The drain line milking apparatus includes an apparatus body comprising a plurality of side opening for receiving a currently connected drain line to milk fluids away from a user, a removable cover disposed over the apparatus body, a circular disk comprising one or more cam openings, a motor to turn the circular disk and one or more circular cams disposed in the one or more cam openings. The circular disk is disposed within the apparatus body.

DETAILED DESCRIPTION

In the following detailed description, numerous specific details are set forth in order to provide a thorough understanding of the embodiments. However, it will be understood by those of ordinary skill in the art that the embodiments may be practiced without these specific details. In other instances, well-known methods, procedures, and components have not been described in detail so as not to obscure the embodiments.

The present embodiments described herein relate to a medical drainage pump such as a drainage pump for milking a drain line (e.g., a drain line milking apparatus or drain line pump). In particular, the present embodiments relate to a portable drain line milking apparatus that may be used at home to reduce a chance of infection in a hospital setting. In some embodiments, the embodiments described herein may be used for a post-surgery drain line such as, but not limited to, a Jackson Pratt drain line. A Jackson Pratt drain is typically a closed system that does not require an outside suction machine and the Jackson Pratt drain line comprises a flexible rubber tube that sits under a patient's skin in an area near an incision. However, sometimes these drain lines do not flow sufficiently and have to be milked. Therefore, the present embodiments may aid in the milking of such drain lines thereby reducing readmittance rates and providing better outcomes for the patient.

Figure 1:
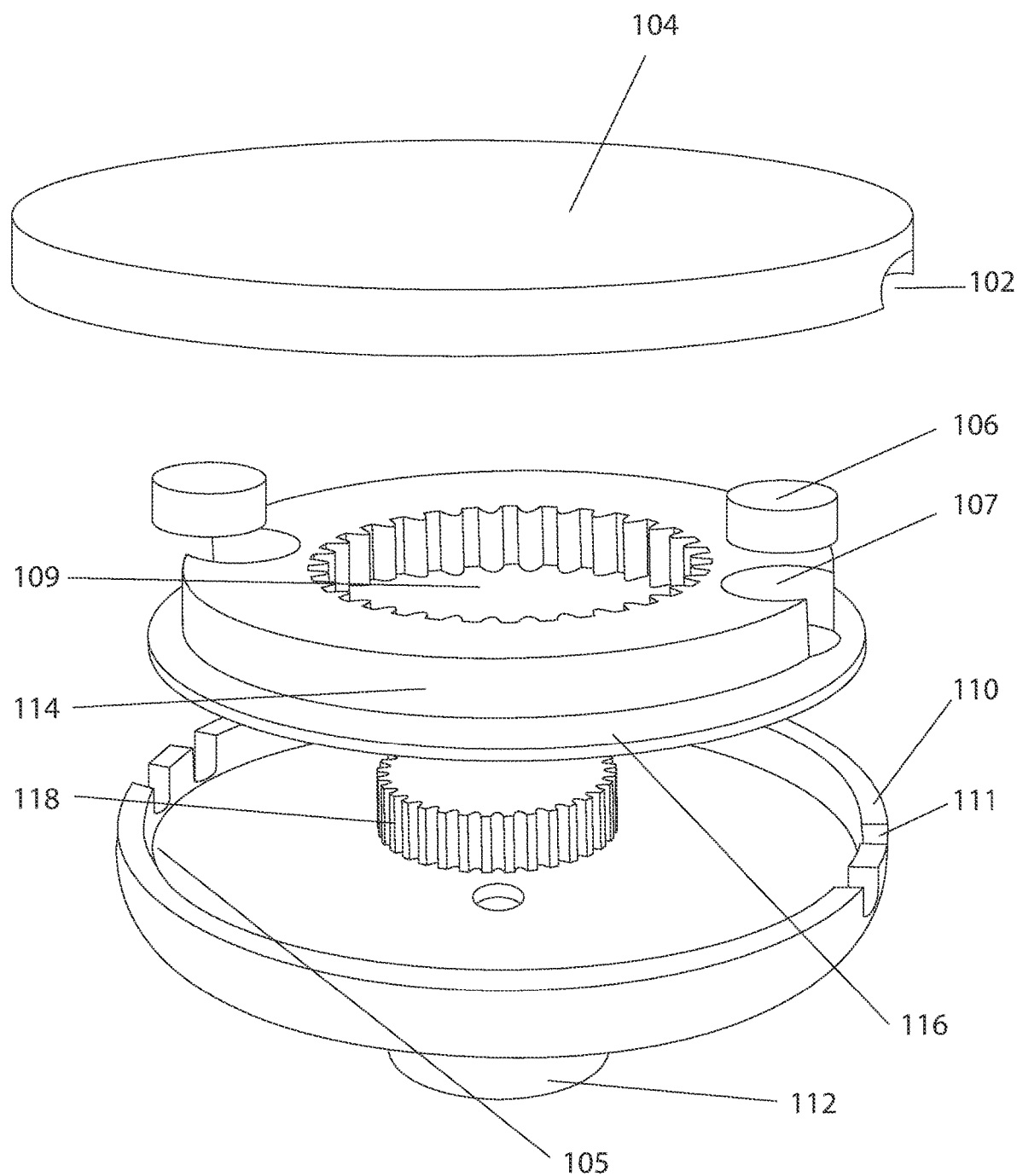
FIG. 1 illustrates a medical drainage pump in accordance with some embodiments.
Figure 2:
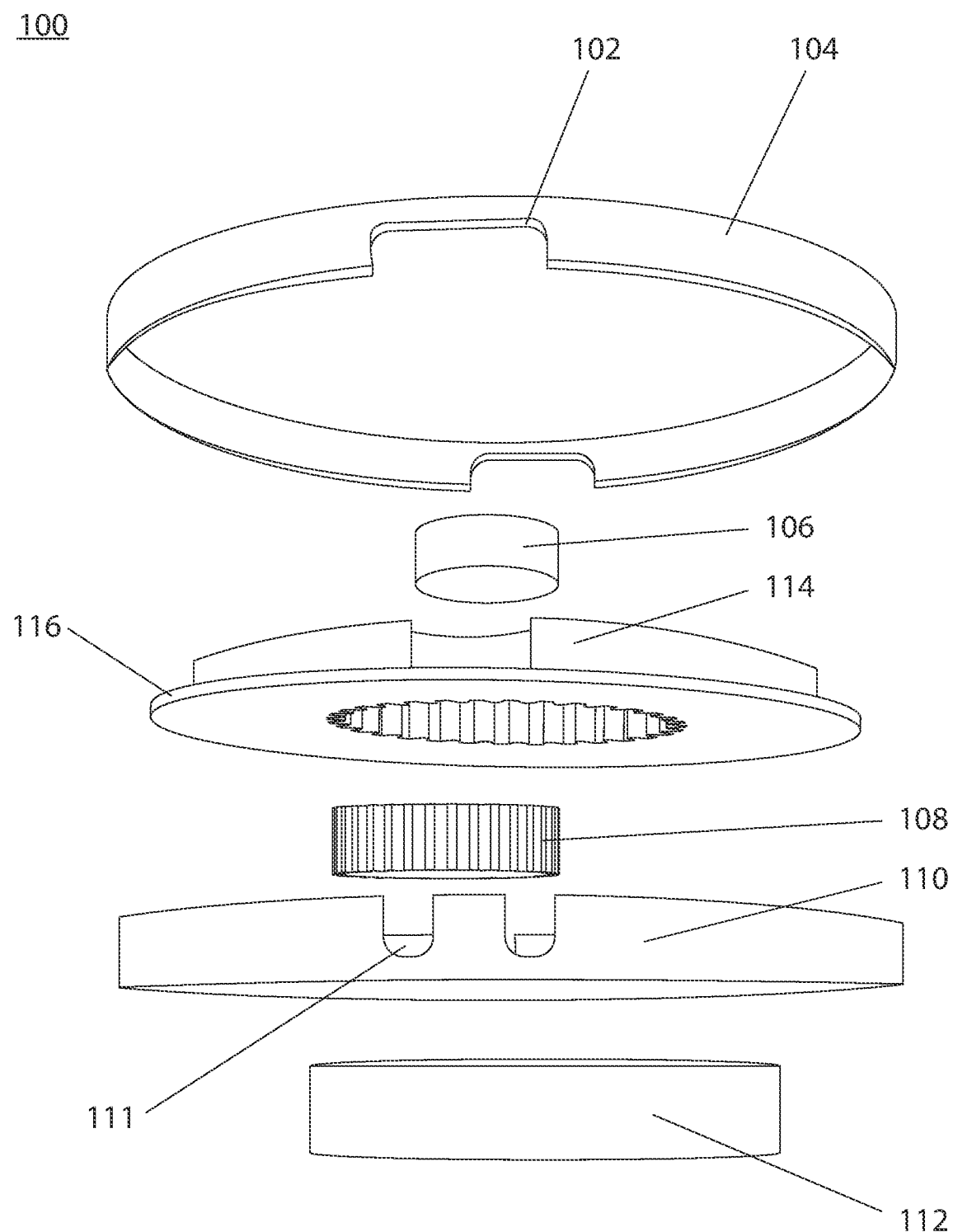
FIG. 2 illustrates a medical drainage pump in accordance with some embodiments.

Referring now to FIG. 1 and FIG. 2, an embodiment of a drain line milking apparatus 100 is illustrated. The drain line milking apparatus 100 may comprise a cover 104 including a cover opening 102 that fits over a body 110 of the drain line milking apparatus 100. The drain line milking apparatus 100 further comprises a one or more cams 106, cam openings 107 that are configured to hold the one or more cams 106. The body 110 may comprise a plurality of body openings 111 and a body interior body wall 105. A circular disk 116 may be disposed on an inside of the body 110 and the circular disk 116 may be rotated using a motor 112, a first gear 118, and second gear 109. The circular disk 116 may include a circular disk exterior wall 114.

The cover 104 may be configured to sit over (i.e., cover) the body 110 while the circular disk 116 is contained within the body 110. The cover may comprise an opening 102 that corresponds to the two or more openings 111 in the body 110. The two or more openings 111 may be used for receiving a drain line and supporting the drain line while the drain line is milked. In some embodiments, the body 110 may be configured with four openings where the openings are aligned in pairs and each pair is opposite of another pair (e.g., 180 degrees apart in a circular configuration).

Figure 3:
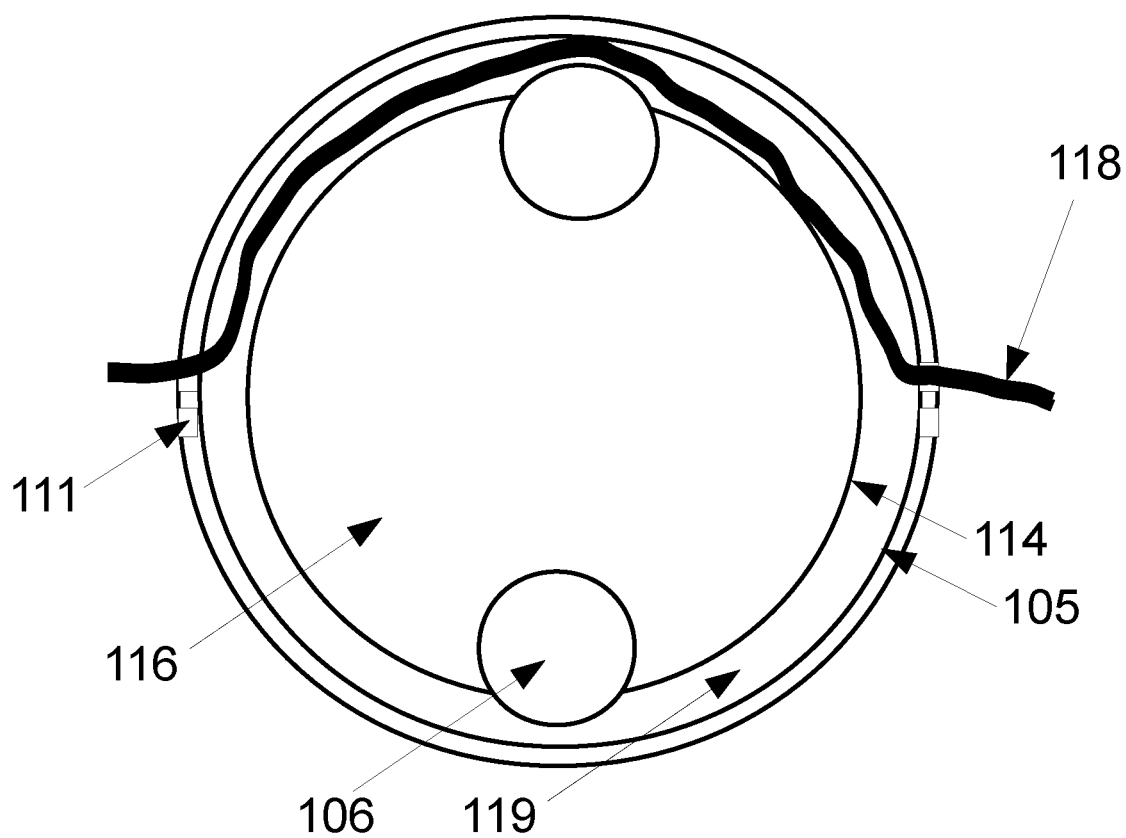
FIG. 3 illustrates a medical drainage pump in accordance with some embodiments.

The circular disk 116 may comprise one or more cam openings 107 that are each configured to hold a cam 106. Each cam 106 may be comprised of a circular disk that rotates within the cam openings 107 as the circular disk 116 turns. The circular disk 116 may comprise an outer edge that is thinner than a central portion of the circular disk where the outer edge of the circular disk extends towards an interior body wall 105. The circular disk 116 may be turned/rotated via the first gear 118 that is driven by a motor 112. In some embodiments, the first gear 118 may be configured to fit inside second gear 109 to turn the circular disk 116. The first gear 118 may be coupled to a shaft (not show) which is turned by the motor 112. In some embodiments, the shaft may be directly coupled to the circular disk 116 without the use of gears. The motor 112 may be an AC or DC powered motor. In some embodiments, the first gear 118 may extend inside the second gear 109 where a central portion of the circular disk 116 defines the second gear 109. Referring now to FIG. 3, an embodiment of a drain line milking apparatus 200 is illustrated. The drain line milking apparatus 200 of FIG. 3, is similar to the drain line milking apparatus 100 of FIG. 1 and FIG. 2. However, and as illustrated in FIG. 3, a drain line 118 is illustrated as entering a first opening 111 and the drain line 118 is disposed in a drain line path 119 that is defined between a side wall of the body 105 and the wall 114 of the circular disk. In some embodiments, the drain line path 119 runs over the outer edge of the circular disk 116. The drain line 118 may exit the body 110 through a second opening 111.

Figure 4:
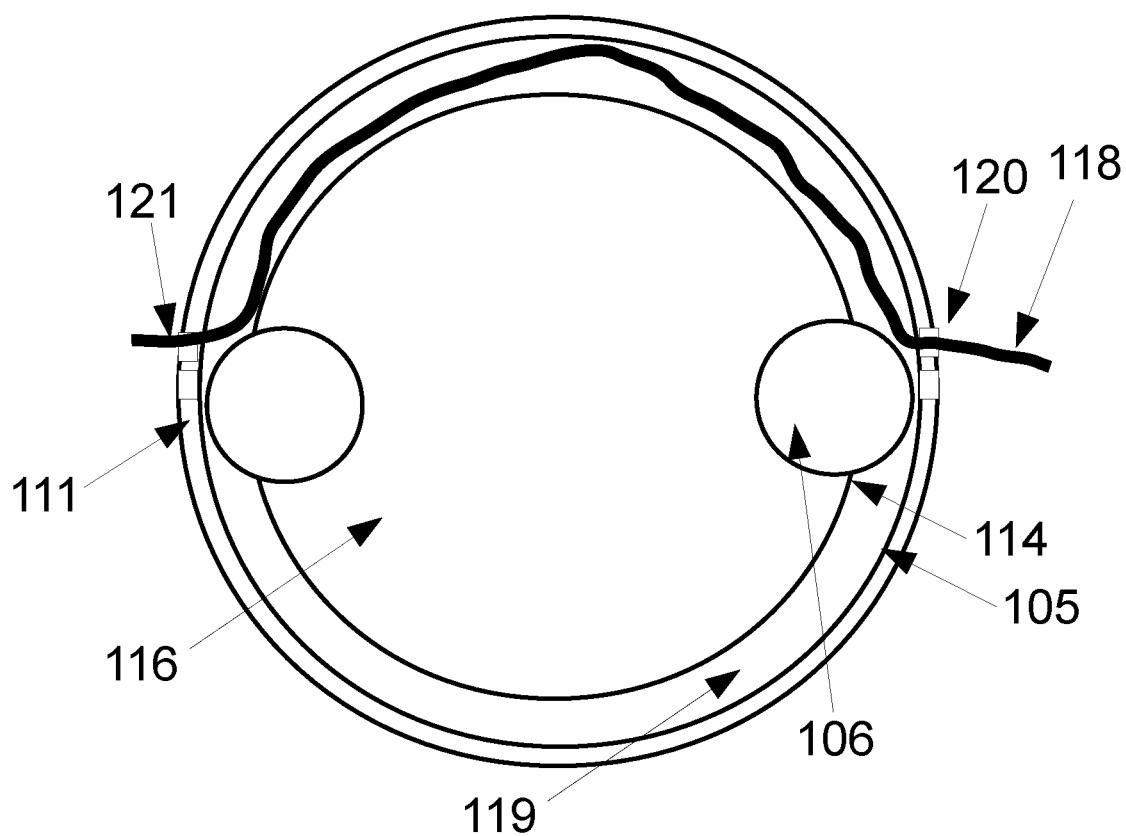
FIG. 4 illustrates a medical drainage pump in accordance with some embodiments.

Referring now to FIG. 4, an embodiment of a drain line milking apparatus 300 is illustrated. The drain line milking apparatus 300 of FIG. 4, is similar to the drain line milking apparatus 200 of FIG. 3. As illustrated in FIG. 4, a drain line 118 is illustrated as entering a first opening 120 and the drain line 118 is disposed in a drain line path 119 that is defined between a side wall of the body 105 and the wall 114 of the circular disk. In some embodiments, the drain line path 119 runs over the outer edge of the circular disk 116. The drain line 118 may exit the body 110 through a second opening 121. In some embodiments, first opening 120 will be less than 180 degrees, and greater than 150 degrees, from second opening 121, to allow for a parking mode so that each cam 106 may be stopped in a position that does not inhibit the flow of a drain line 118. Furthermore, having an opening less than 180 degrees, and greater than 150 degrees apart, allows a drain line to remain as straight as possible while allowing for the cams 106 to be parked (e.g., a parked mode). To engage a park mode, a user may select park on a controller (such as a switch) which instructs to the cams 106, which may be 180 degrees apart, to stop at a location such that neither cam 106 is in physical contact with the drain line 118.

For illustrative purposes, and to aid in understanding features of the specification, an example will now be introduced. This example is not intended to limit the scope of the claims. In some embodiments, a patient that requires surgery during an outbreak of COVID-19, may need to recover from surgery. Due to the high risk of infection from COVID-19, the patient may be instructed to recover at home. As part of the recovery process, the patient may require that a wound be drained and the patient has a drain line installed. The patient may self-monitor his or her drain line. If the person notices that the drain line is not flowing sufficiently, the patient may choose to use a drain line milking apparatus to prevent the drain line from clogging. The patient may then (i) place his drain line through a first opening in a drain line milking apparatus 100, (ii) place the drain line in the drain path 119 and (iii) place the drain line a second opening 111 to exit the milking apparatus. In this fashion, the milking apparatus is never exposed to bodily fluids and can simply be placed over an already installed drain line. This removes any risk of infection that could be introduced by the milking apparatus. The patient may then turn on the motor 112 and the circular disk 116 may spin thus turning each of the cams 106. As the circular disk 116 turns, the cams 106 roll against the drain line 118 pushing the drain line 118 against the wall 105 to apply pressure to the drain line 118. In this manner, the one or more circular cams 106 that are disposed in the one or more cam openings 107, extend past an outer circumference of the circular disk 116 to push the drain line 118 against wall 105. As the cam 106 rolls over the drain line 118, it milks fluid down the drain line and away from the patient. In some embodiments, the motor 112 may be controlled via a timer for setting a length of time that the motor 112 will turn the circular disk 116. If a user has completed milking the drain line 118, the user may set the drain line milking apparatus 100 to a park mode which stops the motor from turning the circular disk 116 once the cams 106 are not contacting the drain line 118. This way the user does not have to remove the drain line from drain line milking apparatus 100 and the cams 106 will not be in contact with the drain line 118.

This written description uses examples to disclose multiple embodiments, including the preferred embodiments, and also to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A drain line milking apparatus comprising:
    an apparatus body comprising a plurality of side openings for receiving a currently connected drain line configured to milk fluids away from a user wherein a first of the plurality of side openings is located less than 180 degrees and greater than 150 degrees from a second of the plurality of side openings;
    a removable cover disposed over the apparatus body;
    a circular disk comprising one or more cam openings, wherein the circular disk is disposed within the apparatus body;
    a motor configured to turn the circular disk; and
    one or more circular cams disposed in the one or more cam openings,
        wherein when the drain line milking apparatus is set to a park mode based on a selection of a switch that instructs the cams to stop at a location such that neither cam is in physical contact with the drain line, the motor is stopped such that the one or more circular cams are not in contact with the currently connected drain line.

2. The drain line milking apparatus of claim 1, wherein, the removable cover comprises a plurality of side cover openings for receiving the currently connected drain line, the plurality of side cover openings corresponding to the plurality of side openings in the apparatus body.

3. The drain line milking apparatus of claim 1, wherein the one or more circular cams, disposed in the one or more cam openings, extend past an outer circumference of the circular disk.

4. The drain line milking apparatus of claim 1, wherein a drain line path is defined between a side wall of the body and the circular disk.

5. The drain line milking apparatus of claim 4, wherein the currently connected drain line is configured to be disposed within the drain line path and wherein when the circular disk turns the one or more circular cams, the one or more circular cams apply pressure on the connected drain line and push the fluids out of the connected drain line.

6. The drain line milking apparatus of claim 1, wherein the fluids in the currently connected drain line enter the apparatus body through the first of the plurality of side openings and exit the apparatus body through the second of the plurality of side openings.

7. A drain line milking apparatus comprising:
    an apparatus body comprising a plurality of side openings for receiving a currently connected drain line configured to milk fluids away from a user, wherein the drain line is a post-surgery drain line where the fluids originate from inside the user;
    a removable cover disposed over the apparatus body, wherein the removable cover comprises a plurality of side cover openings for receiving the currently connected drain line, the plurality of side cover openings corresponding to the plurality of side openings in the apparatus body wherein a first of the plurality of side openings is located less than 180 degrees and greater than 150 degrees from a second of the plurality of side openings;
    a circular disk comprising one or more cam openings, wherein the circular disk is disposed within the apparatus body;
    a motor configured to turn the circular disk; and
    one or more circular cams disposed in the one or more cam openings, wherein the one or more circular cams, disposed in the one or more cam openings, extend past an outer circumference of the circular disk, wherein when the drain line milking apparatus is set to a park mode based on a selection of a switch that instructs the cams to stop at a location such that neither cam is in physical contact with the drain line, the motor is stopped such that the one or more circular cams are not in contact with the currently connected drain line.

8. The drain line milking apparatus of claim 7, wherein, the removable cover comprises a plurality of side cover openings for receiving the currently connected drain line, the plurality of side cover openings corresponding to the plurality of side openings in the apparatus body.

9. The drain line milking apparatus of claim 7, wherein the one or more circular cams, disposed in the one or more cam openings, extend past an outer circumference of the circular disk.

10. The drain line milking apparatus of claim 7, wherein a drain line path is defined between a side wall of the body and the circular disk.

11. The drain line milking apparatus of claim 10, wherein the currently connected drain line is configured to be disposed within the drain line path and wherein when the circular disk turns the one or more circular cams, the one or more circular cams apply pressure on the connected drain line and push the fluids out of the connected drain line.

12. A drain line milking apparatus comprising:
an apparatus body comprising a plurality of side openings for receiving a currently connected drain line configured to milk fluids away from a user wherein a first of the plurality of side openings is located less than 180 degrees and greater than 150 degrees from a second of the plurality of side openings;

a circular disk comprising one or more cam openings, wherein the circular disk is disposed within the apparatus body; and one or more circular cams disposed in the one or more cam openings, wherein when the drain line milking apparatus is set to a park mode based on a selection of a switch that instructs the cams to stop at a location such that neither cam is in physical contact with the drain line, a motor is stopped such that the one or more circular cams are not in contact with the currently connected drain line.

13. The drain line milking apparatus of claim 12, further comprising a removable cover wherein, a removable cover comprises a plurality of side cover openings for receiving the currently connected drain line, the plurality of side cover openings corresponding to the plurality of side openings in the apparatus body.

\* \* \* \* \*